United States Patent [19]
Gibertoni et al.

[11] Patent Number: 6,106,489
[45] Date of Patent: Aug. 22, 2000

[54] CABLE PARTICULARLY FOR TRACHEOSTOMY AND RETROGRADE-INTUBATION TECHNIQUES

[75] Inventors: Lucio Gibertoni, Mirandola; Paolo Bergamaschi, Concordia, both of Italy

[73] Assignee: Mallinckrodt Inc., St. Louis, Mo.

[21] Appl. No.: 09/171,140

[22] PCT Filed: Apr. 4, 1997

[86] PCT No.: PCT/US97/05289

§ 371 Date: Feb. 16, 1999

§ 102(e) Date: Feb. 16, 1999

[87] PCT Pub. No.: WO97/37710

PCT Pub. Date: Oct. 16, 1997

[30] Foreign Application Priority Data

Apr. 11, 1996 [IT] Italy .................................. MI960276 U

[51] Int. Cl.$^7$ ........................................................ A61B 5/12
[52] U.S. Cl. .............................. 600/585; 604/96; 604/280
[58] Field of Search ...................................... 600/585, 433, 600/434; 604/95, 96, 280, 281, 282

[56] References Cited

U.S. PATENT DOCUMENTS 2,118,631   5/1938   Wappler .................................... 604/170
4,244,362   1/1981   Anderson ............................ 128/200.26

Primary Examiner—Cary O'Connor
Assistant Examiner—Pamela L. Wingood
Attorney, Agent, or Firm—Lawrence L. Limpus

[57] ABSTRACT

A cable particularly for tracheostomy and retrograde-intubation techniques, including in combination an elastic guiding wire (2) constituted by a steel wire (3) arranged inside a flexible spring (4) and a traction-resistant steel cord (10) which is rigidly connected to the steel wire (3).

4 Claims, 2 Drawing Sheets

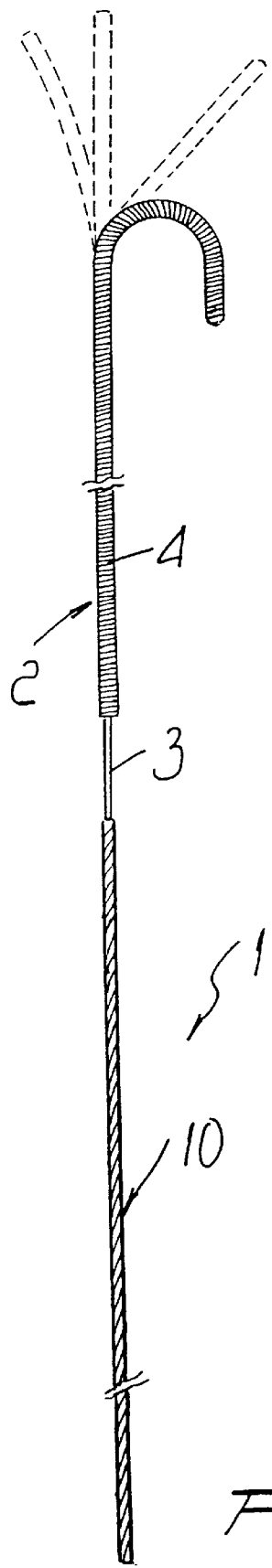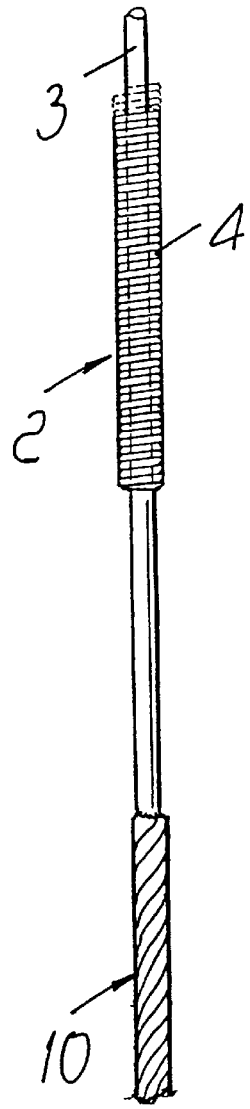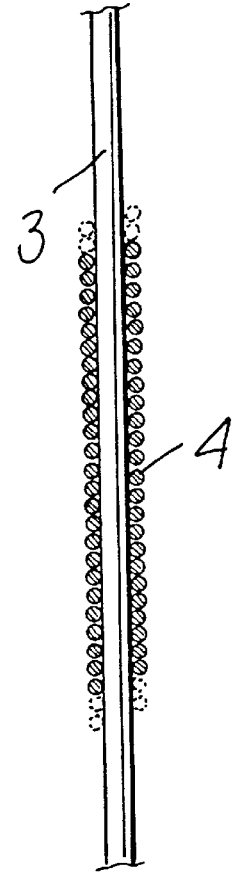

ures and advantages of the invention
CABLE PARTICULARLY FOR TRACHEOSTOMY AND RETROGRADE-INTUBATION TECHNIQUES

TECHNICAL FIELD

The present invention relates to a cable particularly for tracheostomy and retrograde-intubation techniques.

BACKGROUND ART

Conventional nonsurgical or emergency retrograde-intubation and tracheostomy techniques are often based on inserting in the trachea a guiding wire which is inserted through the passage of a needle; dilatation devices are made to slide over said wire, in the case of nonsurgical tracheostomies, or the wire is used as a guiding element for difficult intubations where the tracheal passage is not visible or not easily accessible from the mouth.

The guiding wire being used is substantially provided by means of a spring inside which a steel wire is provided which is folded in a U-like shape at one end, so as to provide a highly flexible element which can be inserted in a needle even in a straight configuration and resume immediately thereafter the U-like shape, which is particularly useful during insertion, since it always tends to regain the axial position and, by being extremely flexible, does not damage the delicate wall of the trachea.

This guiding wire is capable of meeting only some of the technical requirements encountered, since it does not have a sufficient pulling strength and therefore cannot be used whenever it is necessary to perform traction by means of the guiding wire, for example to perform dilation tracheostomies based on the principle of traction, as shown in Italian patent application No. MI 94 A 001043.

Accordingly, when traction has to be applied, it is necessary to use a cable which is constituted by a steel strand, with the consequent additional aid of a rigid tracheoscope, so as to guide the steel cable.

DISCLOSURE OF THE INVENTION

The aim of the invention is to solve the above problem by providing a cable particularly for tracheostomy or retrograde-intubation techniques which allows to combine the flexibility and maneuverability which are typical of an elastic guiding wire with the pulling-strength characteristics which are typical of a steel cord.

Within the scope of this aim, a particular object of the invention is to provide a cable which, while having considerably improved characteristics, does not have a larger diameter than conventional devices.

Another object of the present invention is to provide a cable which, by means of its particular constructive characteristics, is capable of giving the greatest assurances of reliability and safety in use.

A further object of the present invention is to provide a cable particularly for tracheostomy and retrograde-intubation techniques which can be easily obtained starting from commonly commercially available elements and materials and is also competitive from a merely economical point of view.

This aim, these objects, and others which will become apparent hereinafter are achieved by a cable particularly for tracheostomy and retrograde-intubation techniques, according to the invention, characterized in that it comprises in combination an elastic guiding wire constituted by a steel wire arranged inside a flexible spring and a traction-resistant steel cord which is rigidly connected to said steel wire.

BRIEF DESCRIPTION OF THE DRAWINGS

Further characteristics and advantages of the invention will become apparent from the following detailed description of a cable particularly for tracheostomy and retrograde-intubation techniques, illustrated only by way of non-limitative example in the accompanying drawings, wherein:

FIG. 1 is a schematic view of the cable according to the present invention;

FIG. 2 is a view of the connecting region between the steel cord and the steel wire;

FIG. 3 is a schematic view of the guiding wire, illustrating the steel wire inside the flexible spring;

WAYS OF CARRYING OUT THE INVENTION

Figure 4:
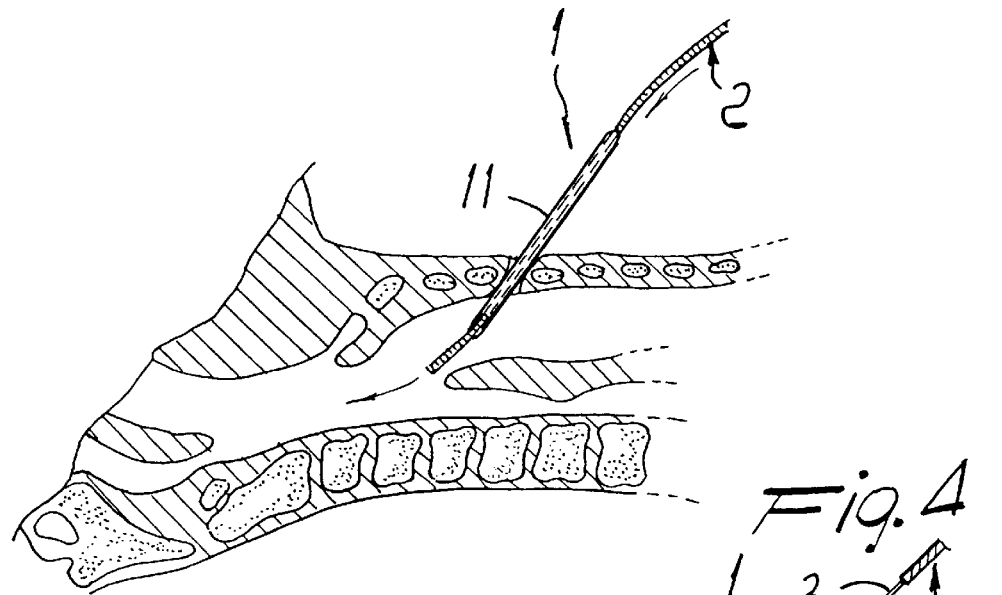
FIG. 4 is a view of the initial step of the insertion of the guiding wire according to the present invention.
Figure 5:
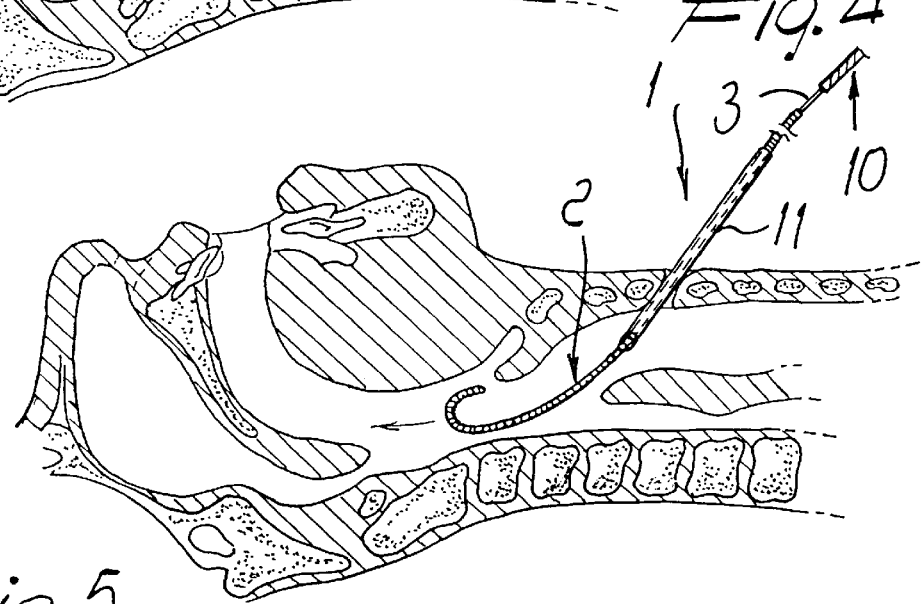
FIG. 5 is a view of the guiding wire inside the trachea.
Figure 6:
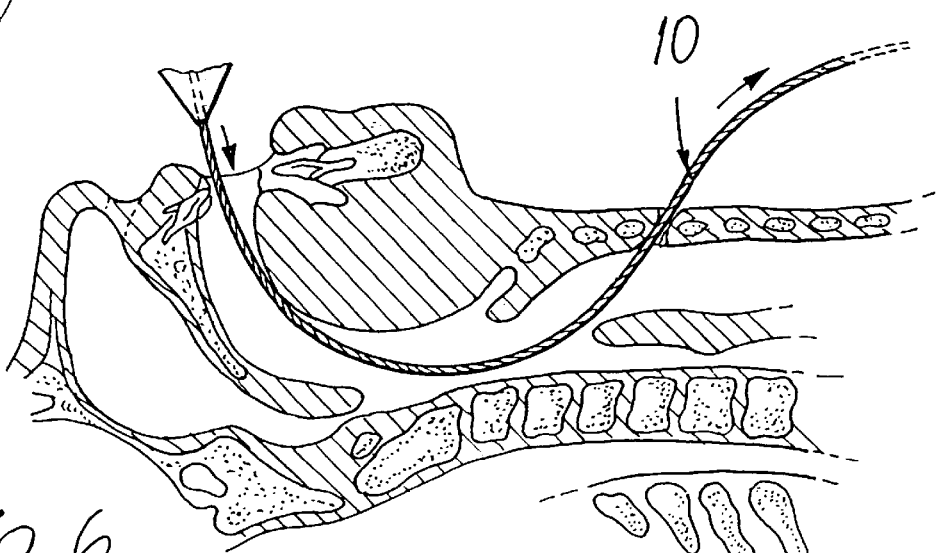
FIG. 6 is a schematic view of the cable when traction is applied to the cord to insert a dilation element inside the trachea.

With reference to the above figures, the cable particularly for tracheostomy and retrograde-intubation techniques, according to the invention, generally designated by the reference numeral 1, comprises, in combination, an elastic guiding wire, generally designated by the reference numeral 2, which is constituted by a steel wire 3 covered by a flexible spring 4 tightly wound around the wire 3.

The steel wire 3 is appropriately rolled at one end so as to make it assume, as shown in FIG. 1, a substantially U-like shape which allows the best penetration and insertion of the guiding wire 2 in the trachea and the like.

At the other end, the steel wire 3 protrudes from the spring 4, and in that region it is rigidly connected to a traction-resistant steel cord 10.

The cord 10, which is provided by means of a steel strand having considerable strength and flexibility, is welded so as to not increase the nominal diameter of the cable 1, thus allowing to easily insert the cable in the passage of a needle 11.

Moreover, all the connecting and welding points are entirely free of protrusions and sharp corners and are entirely rounded and smooth, so as to avoid constituting a source of abrasion or damage to the walls affected by the passage of the medical device.

As illustrated in FIG. 1, in the initial step of the insertion of the guiding wire 2 in the needle 11, the guiding wire, by means of its flexibility and elasticity characteristics, straightens so as to pass through the needle 11; once it has reached the inside of the trachea, it assumes the folded U-shaped configuration at its end, which allows to easily insert the guiding wire 2 in the trachea until it exits from the mouth of the patient.

Once the guiding wire 2 has been inserted, it is possible to apply a slight pulling action until the cord 10, which is rigidly coupled thereto, also exits from the mouth; after cutting, it is possible to connect the cord 10, for example, to a dilation element or in any case to any device whereon it is necessary to apply a pulling action, since the steel-strand cord has adapted dimensions so as to withstand high traction values.

From the above description it is thus evident that the invention achieves the intended aim and objects; in particular, the fact is stressed that a cable is provided which combines the typical advantages of the solutions of the prior art which hitherto had never been combined adequately, namely the flexibility and easy insertion of an elastic guiding wire and the pulling strength of a steel cord.

In practice, the materials employed, so long as they are compatible with the specific use, as well as the contingent shapes and dimensions, may be any according to is requirements.

What is claimed is:

1. A cable, particularly for tracheostomy and retrograde-intubation techniques, comprising in combination an elastic guiding wire constituted by a steel wire arranged inside a flexible spring rolled at one end so as to make it assume a substantially U-like shape, said wire protruding from said spring at its other end and having rigidly attached thereto a traction-resistant steel cord.

2. A cable according to claim 1, wherein said steel wire is connected to said steel cord by welding.

3. A cable according to claim 2, wherein the welding spots between said steel cord and said steel wire are provided so as to have a diameter which is at the most equal to the diameter of the cable.

4. A cable according to claim 1, wherein said steel cord is provided by means of a steel strand.

* * * * *